US006417346B1

(12) United States Patent
Salome et al.

(10) Patent No.: US 6,417,346 B1
(45) Date of Patent: Jul. 9, 2002

(54) PROCESS FOR PREPARING A NONCRYSTALLIZABLE POLYOL SYRUP

(75) Inventors: Jean-Paul Salome, Vieux-Berquin; Patrick Ferez, Lestrem; Philippe Lefevre, Merville, all of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/693,177

(22) Filed: Oct. 20, 2000

(30) Foreign Application Priority Data

Oct. 28, 1999 (FR) .............................. 99 13492

(51) Int. Cl.$^7$ .................. C08B 37/00; C08B 31/00; C07H 1/00
(52) U.S. Cl. ............... 536/104; 536/123.1; 536/123.13; 536/124
(58) Field of Search .............................. 536/104, 123.1, 536/123.13, 124

(56) References Cited

U.S. PATENT DOCUMENTS 3,483,264 A * 12/1969 Tsao ............................ 260/637
5,399,733 A   3/1995  Beitzke et al.
5,773,604 A   6/1998  Lefevre et al.

FOREIGN PATENT DOCUMENTS

| DE | 19612826 | * | 10/1997 |
| FR | 711743 | * | 5/1996 |
| JP | 63079844 | * | 4/1988 |
| SU | 498280 | * | 1/1976 |

OTHER PUBLICATIONS

Abstract in English of JP 41 12212.
Patent abstracts of Japan, vol. 1995, n° p, JP 07 145090.
<European Pharmacopoeia>, 1997, paragraph 0437.

* cited by examiner

Primary Examiner—Ralph Gitomer
Assistant Examiner—Devesh Khare
(74) Attorney, Agent, or Firm—Henderson & Sturm LLP

(57) ABSTRACT

The invention relates to a process for preparing a noncrystallizable polyol syrup stable to heat and to alkaline medium, using a step of hydrogenation of a sugar syrup and a step of caramelization of the hydrogenated sugar syrup, wherein the hydrogenated and caramelized sugar syrup is subjected to purification on ion-exchange resins, the said purification comprising at least one passage over a strong cationic resin at a temperature of less than 50° C., the said temperature being chosen according to the level of reducing sugars desired in the noncrystallizable polyol syrup. It also relates to the use of the polyol syrup obtained for the preparation of toothpastes.

15 Claims, No Drawings

PROCESS FOR PREPARING A NONCRYSTALLIZABLE POLYOL SYRUP

TECHNICAL FIELD

The subject of the invention is a novel process for preparing a noncrystallizable polyol syrup which is stable to heat and to alkalis.

It relates more precisely to a novel process for preparing a polyol syrup which can be used in the manufacture of laundry soaps, detergents, in the formulation of pharmaceutical syrups, of toothpastes, that is to say in any application which requires resistance in alkaline medium and/or in the hot state against the formation of undesirable colours or of inappropriate compounds from the point of view of their taste.

BACKGROUND

Polyols are understood to mean the products obtained by catalytic hydrogenation of simple reducing sugars, of complex reducing sugars such as disaccharides, oligosaccharides and polysaccharides, as well as mixtures thereof, which will be designated in the text which follows by the term "sugar syrup".

In general, the simple reducing sugars which are intended for catalytic hydrogenation according to the invention are glucose, xylose, fructose and mannose. The polyols obtained are then sorbitol, xylitol and mannitol.

The disaccharides are most often maltose, isomaltulose, maltulose, isomaltose and lactose, which lead, through catalytic hydrogenation, to maltitol, isomalt, isomaltitol and lactitol.

Noncrystallizable composition is understood to mean in the present invention the mixtures of polyols which form syrups which are not crystallizable at 20° C. and at a dry matter content of 70% when they are stored in an airtight container for one month. As a guide, the definition of a noncrystallizable sorbitol syrup for the purposes of the invention is in accordance with the European Pharmacopoeia 1997, paragraph 0437.

Sorbitol syrups are widely used in the food, pharmaceutical and chemical sectors. In the formulation of toothpastes and in particular in the manufacture of sodium bicarbonate toothpastes, the use of sorbitol syrups as humectant is only possible if the latter is stable in the presence of sodium bicarbonate, and does not generate a brown colour during storage. Indeed, this colour appears through a reaction of the bicarbonate with the reducing sugars: glucose, maltose, oligo- and polysaccharides. The intensity of the colour increases with the number of polysaccharide units; accordingly, a molecule of maltose generates more colour than a molecule of dextrose. The colour is also greatly accelerated by the temperature to which the syrup is exposed. It has indeed been observed that the same colour intensity is obtained during a storage of 10 days at 45° C. and during a storage of 15 months at 20° C. It is preferable, in addition, for these syrups to be noncrystallizable, so as to facilitate their handling and their transport regardless of the climatic conditions and to ensure the stability over time of the finished products prepared from such syrups.

Maltitol syrups also represent a major class, and are mainly used to prepare noncariogenic food and pharmaceutical products.

Xylitol syrups, although more expensive, have undergone major development because of their high sweetening power, their dental properties and their excellent humectant characteristics.

It is known that the colour of a polyol syrup in the presence of alkalis is linked to the presence of free, reducing sugars: glucose, maltose, oligo- and polysaccharides.

Improving the stability of such syrups therefore requires the elimination of these free sugars.

Several routes have already been envisaged on the laboratory scale.

Japanese patent JP 51 86406 offers perspectives for improving the purity of crystallizable sorbitol syrups using a reduction of crystallized glucose under alkalinity maintained during the entire reduction reaction, with the aim of obtaining sorbitol of high purity, low in nonreduced sugars.

However, this technique remains without practical interest on the industrial scale because it requires the installation of an expensive feeding, control and regulating device, and the constant addition of buffer and of alkaline solution during the reaction penalizes the subsequent purification step. This process is in addition relatively polluting taking into account the large quantities of reagents used. Furthermore, nothing is said on the stability of the sorbitol syrups resulting from the said process.

Japanese patent JP 41 12212 mentions a process for preparing sorbitol of maximum purity which is resistant to heat and to alkalis, which consists in a reduction by addition of hydrogen at high pressure, by envisaging either adjusting the solution to pH 8 to 10 just before the reduction reaction is complete, or heating to a temperature of 60 to 90° C. the sorbitol solution which has been reduced and set at pH 8 to 10 beforehand by means of an alkali, and then after decomposition of the directly residual reducing sugars, in a separation by filtration with or without neutralization with an acid and with or without decolorization on charcoal, and then in a purification on ion-exchange resin.

This process, which applies to a crystallizable sorbitol solution, gives rise to a substantial formation of impurities because of the fact that the reducing sugars are subjected to a relatively long treatment time, of the order of five hours, and does not therefore result in a stability which is judged to be sufficient.

Japanese patent JP 63 79844 and JP 7 145090 describe a process for preparing polyols stable to heat and to alkalis, which consists in treating for one to two hours in the hot state and in an alkaline medium a purified aqueous solution of polyols once by treatment with charcoal and then on ion-exchange resin, and then in purifying once again the solution obtained at 50° C. by passage over an ion-exchange resin. This process applies most particularly to crystallizable sorbitol syrups obtained from glucose syrups of high purity. However, such crystallizable syrups are not appropriate for use in particular in toothpastes because of the many disadvantages which they exhibit. Moreover, this process is found to be particularly complex because of the multiple operations of which it consists, and is therefore difficult to apply on an industrial scale.

Patent EP 0 711 743 (incorporated herein by reference), of which the applicant is the proprietor, describes polyol compositions having a high chemical stability in alkaline medium and a very low reactivity.

These compositions, which are particularly appropriate for use in basic medium requiring an absence of colour, are obtained by catalytic hydrogenation of simple or complex reducing sugars, followed by stabilization and purification of the stabilized syrup.

The stabilizing step consists in subjecting the sorbitol syrups obtained by hydrogenation to oxidation, caramelization or fermentation, so as to bring the syrups to an optical density of less than or equal to 0.100 in an S test.

The applicant had indeed demonstrated that a satisfactory stability could only be achieved at low values in this test, the latter reflecting the colouring capacity of the compositions in alkaline medium.

OBJECTS OF THE INVENTION

In an attempt to further improve the performance of such a process, and with the aim of limiting the inorganic and organic discharges so as to be able to preserve the environment, the applicant then developed, after lengthy research studies, a novel process which makes it possible both to obtain noncrystallizable polyol syrups which are sufficiently stable in alkaline medium, and to easily offer, by limiting the purification operations, a high yield and lesser pollution, which the conventional techniques known in the prior art did not make it possible to obtain.

SUMMARY OF THE INVENTION

Accordingly, the applicant has found that it was appropriate, in order to obtain noncrystallizable polyol syrups stable to heat and to alkalis, to subject a sugar syrup which has been subjected to a hydrogenation and caramelization step, to a purification step on at least one strong cationic resin at a temperature of less than 50° C., the said temperature being chosen according to the level of reducing sugars desired in the final composition.

DETAILED DESCRIPTION

The subject of the invention is therefore a novel process for preparing a noncrystallizable polyol syrup stable to heat and to alkaline medium, using a step of hydrogenation of a sugar syrup and a step of caramelization of the hydrogenated sugar syrup, characterized in that the hydrogenated and caramelized sugar syrup is subjected to purification on ion-exchange resins, the said purification comprising at least one passage over a strong cationic resin at a temperature of less than 50° C., the said temperature being chosen according to the level of reducing sugars desired in the noncrystallizable polyol syrup.

The applicant has indeed demonstrated, after numerous studies, the importance of the working temperature on maintaining the quality of the product during the purification on a strong cationic resin. Indeed, the quality of the composition after purification and in particular its final reducing sugar level is inversely proportional to the temperature for passage over a strong cationic resin.

The purification on a strong cationic resin according to the invention is therefore performed at a temperature of less than 50° C., chosen according to the level of reducing sugars desired in the final composition after purification. Indeed, the applicant has found that the temperature for passage over a resin could be adjusted according to, on the one hand, the level of reducing sugars reached after caramelization and, on the other hand, the final reducing sugar content desired for the purified polyol syrup. This desired content varies according to the applications intended for the syrup. For the preparation of toothpastes, besides the nature of the alkaline agent present in the paste, account should be taken in particular of the nature of the colorants used in order to determine the acceptable limit of resistance to coloration for the polyol syrup. Indeed, a slight yellow colour will be more easily accepted for pastes which are blue in colour. The flavourings used are also a factor to be taken into account in order to determine the acceptable limit of the reducing sugar level. Thus, for some bicarbonate-containing pastes, the acceptable limit is 350 parts per million of reducing sugars (expressed in dextrose equivalent and designated hereinafter by ppm), and for others such as those containing pyrophosphates, levels of up to 500 ppm may be appropriate. This is also applicable for other pharmaceutical, cosmetic or food applications.

Under optimum conditions for carrying out a hydrogenation and then a caramelization of a noncrystallizable polyol syrup, minimum reducing sugar values of the order of 50 to 100 ppm are obtained. Under these conditions, the applicant has found that the maximum temperature at which such a syrup can be purified on a strong cationic resin is 50° C., so as to ultimately obtain, given the increase in the level of reducing sugars in the resins, a value of less than or equal to 500 ppm of reducing sugars which is considered to be the maximum acceptable limit. Below 50° C., it is therefore possible to adjust the temperature for passage over the resin according to the reducing sugar level desired in the final composition and according to the reducing sugar level initially present after caramelization, as will be developed later. Accordingly, the passage over a strong cationic resin may be advantageously adjusted to a temperature of less than or equal to 40° C., preferably of less than or equal to 300° C. and still more preferably of between 20 and 30° C. if a very low reducing sugar level is desired in the polyol composition according to the invention.

The purification itself is carried out based on current practices, that is to say that a passage over a strong cationic resin is first carried out and then over a strong anionic resin, and then over a mixed bed which is a mixture, in equal portion, of these two resins. It is also possible to modify the order of combination of these resins.

The strong cationic resin is designed to remove the cations such as in particular the sodium provided by the sodium hydroxide used during the caramelization, and the soluble nickel provided by the hydrogenation catalyst.

The strong anionic resin is designed to remove the organic anions such as in particular the gluconate, which is a degradation product derived from the caramelization step.

The use, in the final step, of a mixed bed makes it possible to optimize the purification by compensating for possible leaks of ions which might have occurred during the preceding steps.

The use, as cation exchanger, of a strong cationic resin carrying a functional group of the sulphonic $SO_3H$ type used in strong acid form, such as for example the IR 200 C resin marketed by ROHM and HAAS is preferred. As regards the anionic resin, the use of a strong anionic resin such as the IRA 910 resin, marketed by the same manufacturer, is preferred. The mixed bed will consist of a mixture of these two resins.

According to an advantageous embodiment of the process in accordance with the invention, the purification is carried out on resins at a flow rate corresponding to 1.5 times the volume of the resin column through which the syrup passes per hour, this being in order to avoid excessively long residence times in the resin which risk promoting the degradation of the quality of the purified polyol syrup.

According to another advantageous embodiment of the process in accordance with the invention, the caramelization is performed in the hydrogenation reactor, under hydrogen and without separation of the catalyst, by introducing an alkaline agent at the end of the hydrogenation reaction, at a time when the pH is likely to be stable after addition of this alkaline agent without resorting therefore to the use of a buffer.

The applicant has indeed found, after numerous studies, that the hydrogenation step could be advantageously combined with caramelization in the same reactor, without addition of buffer, so as to obtain economically and in a manner which is not very polluting after purification, a polyol composition which is stable in alkaline medium and in the hot state from a sugar syrup.

Caramelization is understood to mean, for the purposes of the present invention, an alkaline degradation of the reducing sugars of the hydrogenate, leading to the formation of corresponding enols. Among the alkaline agents which are quite suitable for the caramelization, the strong or weak bases may be mentioned. According to a preferred embodiment, the alkaline agent used for the caramelization is sodium hydroxide.

The sugar syrup subjected to the process according to the invention may consist in particular of glucose or fructose syrups, of high-maltose glucose syrups or alternatively of xylose syrups.

Advantageously, the sugar syrup consists of 60 to 95% of dextrose, 0.1 to 20% of maltose, the balance for 100 consisting of poly- and oligosaccharides, these percentages being expressed by weight relative to the dry weight of the saccharides contained in the said syrup.

The catalytic hydrogenation is carried out in a manner known per se, in a jacketed reactor, on Raney nickel catalysts, any other catalyst for hydrogenation of sugars being appropriate.

Preferably, it is carried out at a hydrogen pressure of between 30 and 100 bar, at a temperature of between 120 and 150° C., and more preferably still at a temperature of between 130 and 150° C., this being in order to optimize the rate of hydrogenation while limiting the side reactions thereof.

Sodium hydroxide is introduced into the reactor so as to obtain a pH of between 9 and 11, preferably of between 9.5 and 11, at a time when the latter is sufficiently stable so as not to resort to a buffer solution or so as not to have to add a massive quantity of sodium hydroxide in order to maintain the pH at this value. This stage is generally reached after 1 hour 30 minutes of hydrogenation, under the conditions in accordance with the invention.

This criterion for introducing sodium hydroxide results from the study of the kinetics of hydrogenation and of the caramelization conditions. When the reaction medium is still rich in free reducing sugars, the introduction of the alkaline agent causes an instability of the pH which drops substantially because of the conversion of these free reducing sugars to the corresponding acids. Thus, above a reducing sugar content of about 0.4%, an excessive formation of acids is observed and therefore a drop in pH, making the stabilizing action of the caramelization ineffective and involving an excessive addition of sodium hydroxide. It is therefore preferable to introduce the alkaline agent when the residual reducing sugar content is less than 0.2%, and more preferably still less than or equal to 0.1%.

When the pH in the reactor is less than 9, the caramelization is insufficient. When it is greater than 11, the caramelization is sufficient but the ionic charge of the hydrogenate becomes too high, which causes a substantial discharge of chlorides during the regeneration of the cation-exchange ratings. At a pH of between 9.5 and 11, the applicant observed that the excess of sodium hydroxide in the reaction medium was sufficient to ensure complete caramelization of the sugars.

The process in accordance with the invention makes it possible to obtain polyol syrups which are particularly suitable for use in the preparation of products having a basic pH such as, in particular, toothpastes based on sodium bicarbonate or on the sodium phosphate family, antacid compositions, shaving foams, depilatory creams, or for the manufacture of products at high temperature, while achieving a profitability which has so far been unrivalled, and a minimal level of organic and inorganic discharges.

According to an advantageous embodiment of the process in accordance with the invention, the syrup obtained is a noncrystallizable sorbitol syrup.

Preferably, the noncrystallizable sorbitol syrup obtained has a sorbitol content of at least 64% by weight, a maltitol content of at least 6% by weight, the oligo- and polysaccharide content constituting the balance for 100%, these percentages being expressed relative to the dry matter content of the polyols present in the composition.

The syrup which can be obtained according to the process in accordance with the invention can thus be advantageously used in the preparation of products at a basic pH, containing alkaline agents, or treated or obtained at high temperature.

The subject of the invention is also a toothpaste containing the polyol syrup which can be obtained according to the process in accordance with the invention.

The invention will be illustrated with the aid of the examples which follow and which are given without limiting the scope of the invention.

EXAMPLE 1

Into a jacketed reactor having a capacity of 20 liters, containing Raney nickel in suspension, there is introduced, with stirring, a sugar syrup whose composition is the following:

dextrose: 75% on a dry basis maltose: 8% on a dry basis maltotriose: 3.6% on a dry basis higher DP values: 13.4% on a dry basis The dry matter content of the reaction medium is 40% by weight, and the Raney nickel content is 5% by weight, expressed relative to the dry weight.

The hydrogenation is carried out for 1 h 30 min at a pressure of 50 bar and a temperature of 140° C.

A 3% sodium hydroxide solution by weight is then introduced over 15 minutes so as to bring the pH of the hydrogenate to a value of 10.8. It is observed that the pH is stable, the reducing sugar content being less than 0.4% by weight.

The hydrogenation is continued for 20 minutes.

After that, the stirring of the reactor is stopped, the mixture is allowed to settle out for 15 minutes and the supernatant is emptied into a decanter in order to recover the catalyst. The supernatant in the decanter is then filtered in order to remove the last traces of catalyst.

The syrup thus obtained is then subjected, after having cooled it to 25° C., to a purification on a strong cationic resin, and then on an ionic resin, and then on a mixed bed.

The syrup obtained is then subjected to a test of stability to the alkaline agents. This test, termed S test, is described in patent EP 711 743 of which the applicant is the proprietor. The lower the value obtained in this S test (optical density less than 0.1), the higher the stability of the polyol compositions.

500 mg of sodium hydrogen carbonate of ultrapure quality, and 250 mg of a 20% aqueous solution of ammonia are added to 5 ml of syrup.

The whole is mixed and heated for 2 hours on a water bath at 100° C., without stirring.

The solution is cooled to 20° C. and the optical density thereof is measured at a wavelength of 420 nm, with the aid of a spectrophotometer such as the one marketed by PERKIN-ELMER under the trademark Lambda 5 UV/VIS Spectrophotometer.

In the same manner, a calibration series is prepared by replacing the 5 ml of syrup with 3 ml of pure water and 2 ml of anhydrous pure glucose solutions, having the concentration 100, 200, 300, 400, 500, 600 and 1000 parts per million.

The absorbence of these glucose solutions is: 0.04, 0.08, 0.120, 0.160, 0.205, 0.250 and 0.413, respectively.

A relatively low optical density, of 0.04, is obtained for the syrup obtained in accordance with the present invention.

This is equivalent to a glucose titre of 100 parts per million on a dry basis, which is a value indicative of a very high stability to alkalis.

The process in accordance with the invention therefore makes it possible to obtain more economically and in a less polluting manner than the prior art techniques a noncrystallizable polyol composition which is very stable in alkaline medium and/or in the hot state.

EXAMPLE 2

Influence of the Temperature on the Purification by Means of Ion-exchange Resins The syrup obtained according to Example 1 is taken before purification and divided into seven fractions.

These fractions are purified on a strong cationic resin, at 20, 30, 35, 40, 45, 50, 52 and 60° C., respectively (fractions identified from A to H), and then on an anionic resin and finally on a mixed bed.

An S test is performed on each fraction after purification and the difference with the initial test (delta S test) is calculated for each point.

The results are given in parts per million dextrose equivalent.

| PURIFICATION TEMPERATURE | FRACTION | Reducing sugar level after purification expressed in ppm dextrose equivalent | Increase in the reducing sugar level (in ppm dextrose equ.) |
|---|---|---|---|
| 20° C. | A | 100 | 0 |
| 30° C. | B | 200 | 100 |
| 35° C. | C | 260 | 160 |
| 40° C. | D | 350 | 250 |
| 45° C. | E | 450 | 350 |
| 50° C. | F | 560 | 460 |
| 52° C. | G | 600 | 500 |
| 60° C. | H | 950 | 850 |

These results clearly demonstrate the influence of the working temperature during the purification on a strong cationic resin. It is thus shown that it is possible to adjust the temperature of the composition during its purification, according to the requirements in relation to reducing sugars which the final application envisaged requires, which gives the process according to the invention a flexibility which did not exist up until now.

EXAMPLE 3

Formulation of a Toothpaste Containing Sodium Bicarbonate

A toothpaste containing sodium bicarbonate is produced with products A and F of Example 2 (purified on resins at 20° C. and at 50° C.) according to the following formula:

|  | PASTE A | PASTE B |
|---|---|---|
|  | (% by weight) | |
| Syrup A | 45.00 | |
| Syrup F | | 45.00 |
| Sodium bicarbonate | 10.00 | 10.00 |
| Abrasive silica Tixosil 73 | 9.00 | 9.00 |
| Abrasive silica Tixosil 43 | 10.00 | 10.00 |
| Sodium lauryl sulphate (30% aqueous solution) | 5.66 | 5.66 |
| Sodium monofluorophosphate | 0.80 | 0.80 |
| Sodium carboxymethylcellulose | 0.70 | 0.70 |
| Titanium dioxide | 0.70 | 0.70 |
| Mint flavour | 1.00 | 1.00 |
| Purified water | qs 100.00 | id |
| Sodium saccharinate | 0.2 | 0.2 |

The toothpastes A and B obtained have a pH of 8.4 and 8.7, respectively, in a 10% solution.

After storing for 6 months at room temperature, the colour of the paste A did not change because of the satisfactory purity of product A.

The paste B has, by contrast, an unacceptable yellowish colour after the same storage time.

EXAMPLE 4

Formulation of Anti-tartar Toothpastes with Sodium Pyrophosphate

An anti-tartar toothpaste is prepared with sodium pyrophosphate as anti-tartar agent, and product D of Example 2 (purified on a strong cationic resin at 40° C.), according to the following formula:

| Syrup D | 45.00 |
|---|---|
| Sodium pyrophosphate | 4.00 |
| Abrasive silica TIXOSIL 73 | 9.00 |
| Thickening silica TIXOSIL 43 | 11.00 |
| Sodium saccharinate | 0.20 |
| Methyl para-hydroxybenzoate | 0.18 |
| Propyl para-hydroxybenzoate | 0.02 |
| Titanium dioxide | 0.70 |
| Sodium carboxymethylcellulose | 0.70 |
| Sodium monofluorophosphate | 0.76 |
| Sodium lauryl sulphate (30% aqueous soln.) | 5.66 |
| Mint flavour | 1.00 |
| Purified water qs | 100.00 |

The final pH of the toothpaste is 7.8 as it is and 8.6 after 10% dilution.

After storing the toothpaste for six months at room temperature, no modification of its colour appears.

The syrup D of Example 2 is therefore quite appropriate for use in a toothpaste in the presence of an anti-tartar agent.

What is claimed is:

1. A process for preparing a noncrystallizable polyol syrup stable to heat and to alkaline medium, using a step of hydrogenation of a sugar syrup and a step of caramelization of the hydrogenated sugar syrup, wherein the hydrogenated and caramelized sugar syrup is subjected to purification on ion-exchange resins, the said purification comprising at least one passage over a strong cationic resin at a temperature of less than 50° C., the said temperature being chosen according to the level of reducing sugars desired in the noncrystallizable polyol syrup.

2. The process according to claim 1, wherein the caramelization treatment is performed in the hydrogenation reactor, under hydrogen and without separation of the catalyst, by introducing sodium hydroxide at the end of the hydrogenation reaction.

3. The process according to claim 1, wherein the caramelization step consists in bringing the pH of the hydrogenated syrup to a value of between 9 and 11, when this pH is likely to be stable.

4. The process according to claim 3, wherein the caramelization step consists in bringing the pH of the hydrogenated syrup to a value of between 9.5 and 11, when this pH is likely to be stable.

5. The process according to claim 1, wherein the purification step is performed on a strong cationic resin at a temperature of less than 50° C., and then on an anionic resin and finally on a mixed bed.

6. The process according to claim 1, wherein the temperature for passing over a strong cationic resin is less than or equal to 40° C.

7. The process according to claim 6, wherein the temperature for passing over a strong cationic resin is less than or equal to 30° C.

8. The process according to claim 6, wherein the temperature for passing over a strong cationic resin is of between 20° C. and 30° C.

9. The process according to claim 1, wherein the polyol syrup is a noncrystallizable sorbitol syrup.

10. The process according to claim 9, wherein the noncrystallizable sorbitol syrup has a sorbitol content of at least 64% by weight, a maltitol content of at lest 6% by weight, the oligo- and polysaccharide content constituting the balance for 100%, these percentages being expressed relative to the dry matter content of the polyols present in the composition.

11. In a process for the preparation of products at a basic pH, containing alkaline agents, either treated or obtained at high temperature, the improvement consisting of using a polyol syrup obtained according to a process in accordance with claim 1.

12. A toothpaste composition containing the polyol syrup obtained according to a process in accordance with claim 1.

13. A laundry soap composition containing the polyol syrup obtained according to a process in accordance with claim 1.

14. A detergent composition containing the polyol syrup obtained according to a process in accordance with claim 1.

15. A pharmaceutical syrup composition containing the polyol syrup obtained according to a process in accordance with claim 1.

* * * * *

UNITED STATES PATENT AND TRADEMARK OFFICE
CERTIFICATE OF CORRECTION

PATENT NO.   : 6,417,346 B1
DATED        : July 9, 2002
INVENTOR(S)  : Jean-Paul Salome, Patrick Ferez and Philippe Lefevre It is certified that error appears in the above-identified patent and that said Letters Patent is hereby corrected as shown below:

Column 4,
Line 25, please correct as follows:
-- 30° C. and still more preferably of between 20 and 30° C. --

Signed and Sealed this

Twenty-third Day of September, 2003

JAMES E. ROGAN
*Director of the United States Patent and Trademark Office*